United States Patent [19]

Howland

[11] Patent Number: 5,653,708
[45] Date of Patent: Aug. 5, 1997

[54] CERVICAL SPINE ROD FIXATION SYSTEM

[75] Inventor: Robert S. Howland, Seal Beach, Calif.

[73] Assignee: Advanced Spine Fixation Systems, Inc., Irvine, Calif.

[21] Appl. No.: 303,580

[22] Filed: Sep. 9, 1994

Related U.S. Application Data

[63] Continuation of Ser. No. 998,116, Dec. 28, 1992, abandoned

[51] Int. Cl.$^6$ .................................................. A61B 17/70
[52] U.S. Cl. .................................................. 606/61; 606/73
[58] Field of Search .................................. 606/61, 57, 73, 606/105, 60, 53, 54, 59, 72

[56] References Cited

U.S. PATENT DOCUMENTS

| | | | |
|---|---|---|---|
| 4,483,334 | 11/1984 | Murray . | |
| 4,653,481 | 3/1987 | Howland et al. . | |
| 4,719,905 | 1/1988 | Steffee . | |
| 4,772,448 | 9/1988 | Popalis et al. . | |
| 5,000,165 | 3/1991 | Watanabe . | |
| 5,024,213 | 6/1991 | Asher et al. . | |
| 5,030,220 | 7/1991 | Howland | 606/61 |
| 5,084,048 | 1/1992 | Jacob et al. | 606/61 |
| 5,176,679 | 1/1993 | Lin | 606/61 |
| 5,196,013 | 3/1993 | Harms et al. | 606/61 |
| 5,209,752 | 5/1993 | Ashman et al. | 606/61 |
| 5,217,497 | 6/1993 | Mehdian | 623/17 |
| 5,242,444 | 9/1993 | MacMillan | 606/61 |
| 5,242,445 | 9/1993 | Ashman | 606/61 |
| 5,254,118 | 10/1993 | Mirkovic | 606/61 |

FOREIGN PATENT DOCUMENTS

| | | |
|---|---|---|
| 0408489 | 1/1991 | European Pat. Off. . |
| 0425783 | 5/1991 | European Pat. Off. . |
| 468264 | 1/1992 | European Pat. Off. ............... 606/61 |
| 0553782 | 8/1993 | European Pat. Off. . |
| 9111967 | 8/1991 | WIPO . |

OTHER PUBLICATIONS

William L. Carson, Ph.D., "Biomechanical Overview of the Isola Modular Spine Implant System, An Introduction", Sep. 16, 1989, Columbia, Missouri, pp. 1–26.

AcroMed Corporation, "Kaneda Anterior Spinal Instrumentation System Technique Manual", pp. 1–22. Date unknown, author unknown.

DIMSO, "Spinal Fixation Diapason Device and Technique", pp. 1–5. Date unknown Author unknown.

Sofamor Division Raquis, "Compact CD Low Back" Catalogo de los Productos, Brochure. Date unknown, author unknown.

*Primary Examiner*—Guy V. Tucker
*Attorney, Agent, or Firm*—Christie, Parker & Hale, LLP

[57] ABSTRACT

A cervical spine fixation system is described. The fixation system comprises a bone screw for implanting in the cervical vertebrae of the spine and for accommodating a clamping assembly. The clamping assembly comprises a rod receiving aperture which is angularly oriented a predetermined amount from perpendicular with respect to a longitudinal axis of the bone screw.

8 Claims, 13 Drawing Sheets

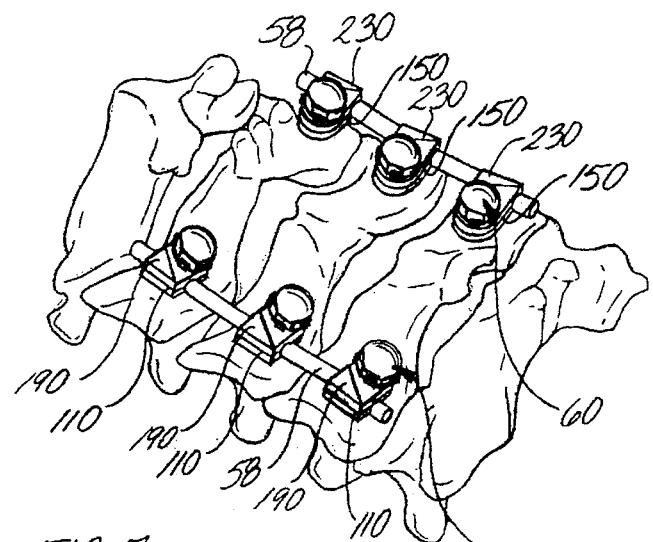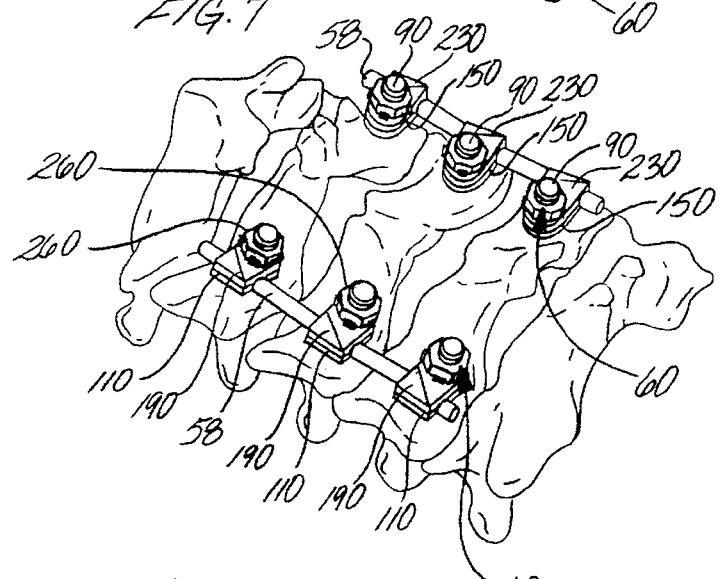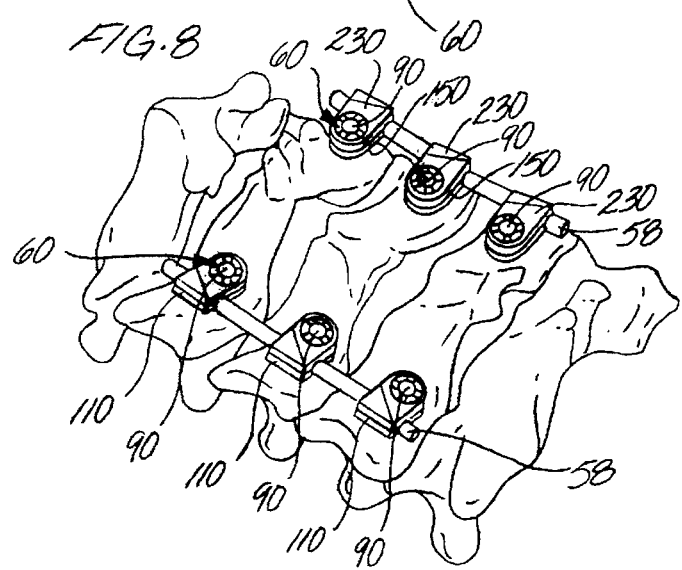

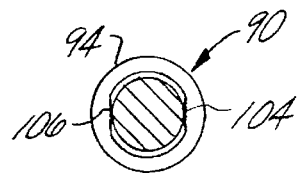
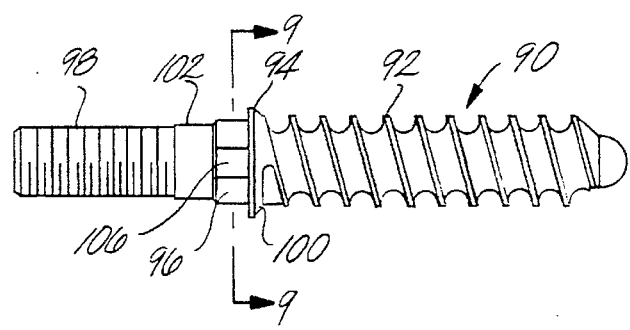
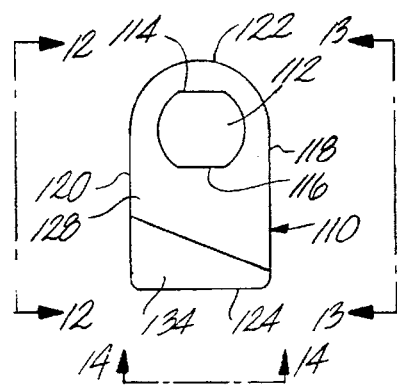
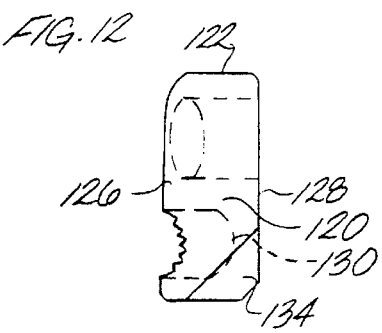
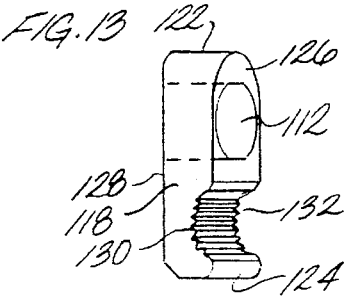

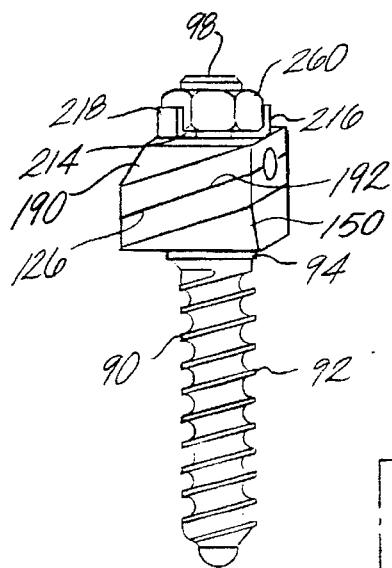
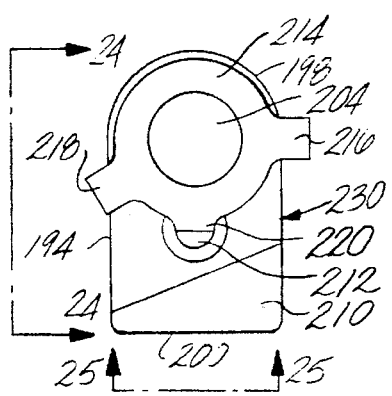
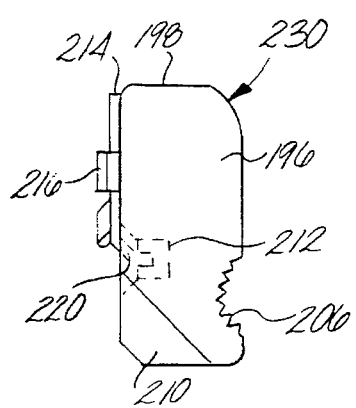
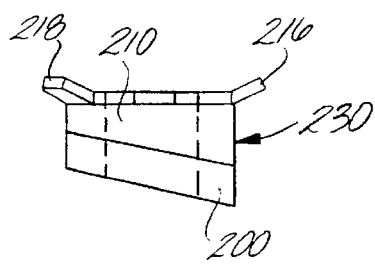
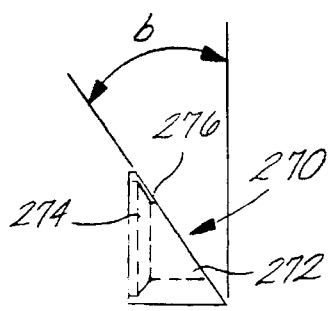
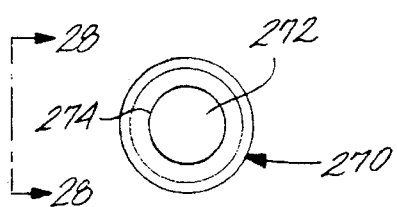

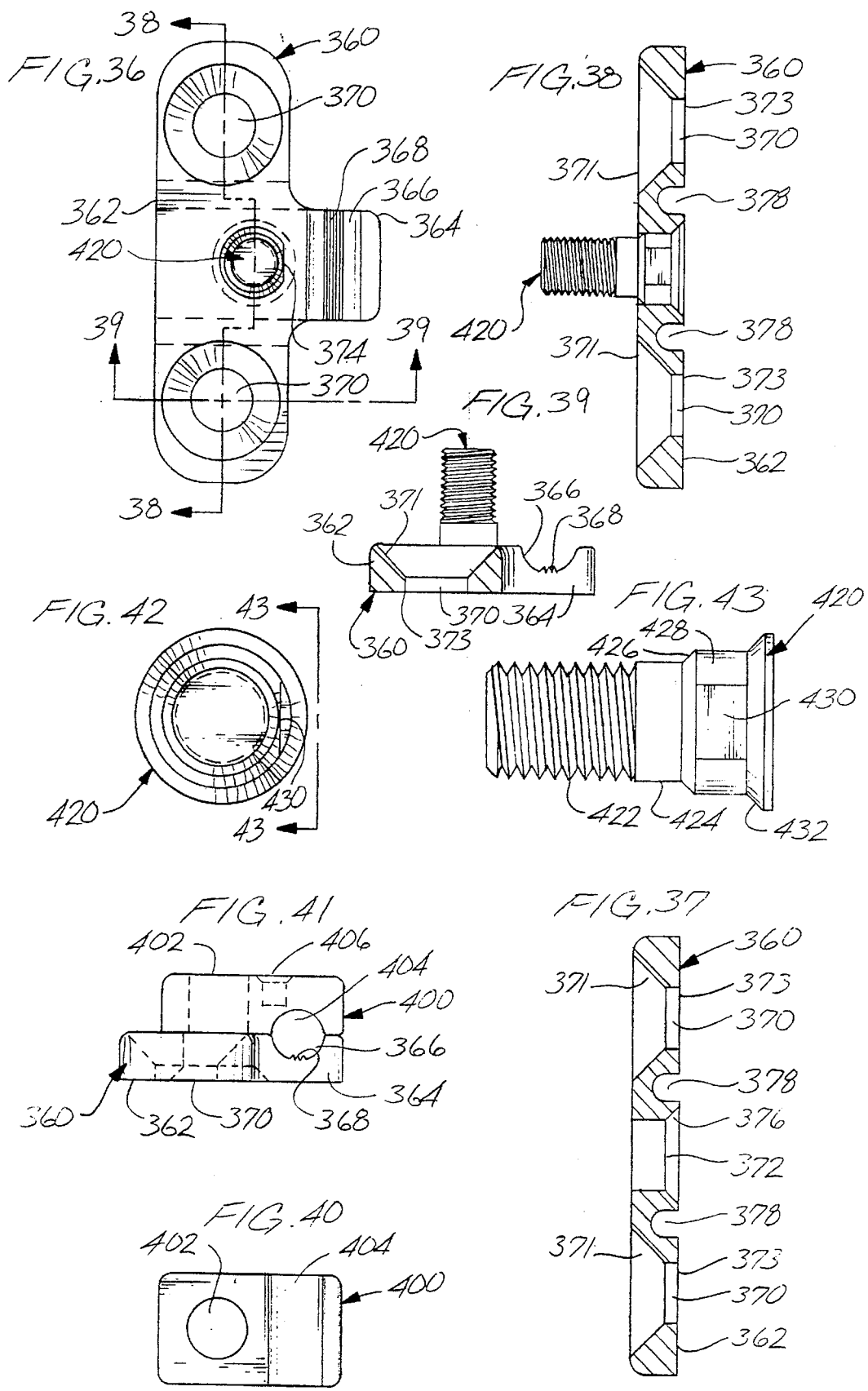

CERVICAL SPINE ROD FIXATION SYSTEM

CROSS-REFERENCE TO RELATED APPLICATION

This is a continuation of application Ser. No. 07/998,116, filed Dec. 28, 1992, now abandoned.

FIELD OF THE INVENTION

The present invention relates to instrumentation for fixation of the cervical region of the spine and more particularly to implantable cervical spine screw and rod fixation systems.

BACKGROUND OF THE INVENTION

Every year there are a significant number of people who suffer severe neck injuries from trauma. These injuries include cervical fractures, fracture dislocations combined with retropulsion of the disc and other major injuries. Also, each year many people undergo cervical spine surgery for degenerative diseases, especially degenerative spinal stenosis, which involves the removal of much of the bone which supports the cervical region of the spine resulting in instability of the cervical region.

Treatment of these conditions has included traction either with a halter or with Crutchfield type tongs followed by application of a cast or brace. If surgery is necessary, the area of injury is often fixed with wire to allow fusion of the vertebrae in the affected region of the vertebral column. Often the treatment includes anterior decompression and fusion, or more recently, plates and screws have been used to immobilize the unstable region. Such plates may be used either anteriorly or posteriorly, or in a few cases, both anteriorly and posteriorly.

While these fixation devices have been used effectively, they have a number of serious disadvantages. For example, the use of wires prevents flexion, as required for effective fixation, but does not prevent rotation nor extension of the cervical region, which leads to poor fixation of the vertebrae in this region. Currently, wires are nearly always used in combination with bone grafts. Sometimes the grafts are placed between the posterior elements of the vertebrae in such a fashion as to prevent extension, and since the wires prevent flexion, some stabilization is obtained. However, the stabilization is usually insufficient to avoid the necessity for the additional stability conferred by the use of halo devices, large casts or braces.

In the case where posterior plates and lateral bone mass screws are used, the stability is increased by simply screwing the plate into the bone. However, since the bone in the cervical area is relatively soft, the screws of such devices easily pull or cut out of the bone and, therefore, do not immobilize well. Even if there is no major failure of the device, such as the screws pulling out of the bone, the screws eventually work loose and plates, that initially prevented all motion, tend to loosen as the patient recovers from the surgery and becomes more active. As a result, halos, casts and braces are often used in conjunction with screw and plate fixation.

Numerous fixation devices have been described, such as those described in U.S. Pat. Nos. 5,030,220 and 5,034,011, for use in the lumbar-sacrum regions of the spine. While these fixation devices have proven successful for use in the lumbar region, the physiology and structure of the cervical spine, C1 to C7, is very different from the lumbar-sacrum regions. For example, the bone screws, when placed in the lateral masses of the cervical vertebra, are usually placed at an angle from horizontal, whereas in the lumbar region they are placed in a horizontal plane. However, for proper stabilization and fixation, the hardware carried by the bone screws ought be such as to provide support and stabilization, generally along the axis of the cervical portion of the spine, rather than at an angle to it. It is desirable that a cervical fixation device be developed which would preferably take into account these considerations. In addition, it is desirable that a cervical fixation device be relatively compact and easy to install.

SUMMARY OF THE INVENTION

A cervical spine fixation system is described for the correction and stabilization of the spine in the cervical region. The fixation system comprises a bone screw wherein one end of the bone screw is implanted in a cervical vertebrae of the spine and the other end of the bone screw accommodates a clamping assembly.

The clamping assembly comprises a rod receiving aperture angularly oriented a predetermined amount from perpendicular with respect to a longitudinal axis of the bone screw.

In one embodiment of the present invention the clamping assembly comprises an upper and a lower saddle which, when assembled on the bone screw, the upper and lower saddles mate, in parallel relation, to form the rod-receiving aperture. Means are provided for attaching the clamping assembly to the bone screw.

The attachment of the clamping assembly to the bone screw provides means for clamping the rod receiving aperture onto a rod located in the aperture. When installed, the clamping assemblies located on adjacent vertebrae are connected by a rod which is clamped in the rod receiving aperture, thus preventing rotation of the clamped vertebrae, relative to each other. The installation of the system is generally performed on both sides of a single vertebrae.

In one embodiment of the present invention a sleeve, nut which is substantially recessed into the clamping assembly when the bone screw and clamps are assembled, is used to attach the clamping assembly to the bone screw. In another embodiment the means of attachment comprises a lock washer having a plurality of spaced tangs mounted on the upper surface of the upper saddle wherein one of the tangs of the lock washer is received in an aperture to secure the lock washer to the upper saddle.

DESCRIPTION OF THE DRAWINGS

Features, aspects and advantages of the present invention will be more fully understood when considered with respect to the following detailed description, appended claims and accompanying drawings wherein:

FIG. 6 is a view similar to FIG. 5 illustrating the completed assembly in accordance with one embodiment of the present invention;

FIG. 7 is a view similar to FIG. 5 illustrating the completed assembly in accordance with a second embodiment of the present invention;

FIG. 8 is a view similar to FIG. 5 illustrating the completed assembly in accordance with a third embodiment of the present invention;

FIG. 9 is a view, in section, of a bone screw taken along the line 9—9 of FIG. 10;

FIG. 10 is a side view of a bone screw in accordance with the present invention;

FIG. 11 is a plan view of the bottom surface of the lower left hand saddle;

FIG. 12 is a side view taken along the line 12—12 of FIG. 11;

FIG. 13 is a side view taken along the line 13—13 of FIG. 11;

FIGS. 23, 24, and 25 are views similar to FIGS. 20, and 22 but illustrating an upper right hand saddle on which a lock washer is secured;

FIG. 26 is a perspective view, as seen from the front face, on the same side as the rod receiving aperture, illustrating the mating fit of the upper and lower left saddles;

FIG. 27 is a plan view of a cervical screw spacer in accordance with the present invention;

FIG. 28 is a side view of the spacer taken along line 28—28 of FIG. 27;

FIG. 36 is a plan view of a lower occipital plate;

FIG. 37 is a side view taken along line 38—38 of FIG. 36 of the plate of FIG. 36 without an occipital plate stud assembled into the lower occipital plate;

FIG. 38 is a side view taken along line 38—38 of FIG. 36 of the plate of FIG. 36 with an occipital plate stud assembled into the lower occipital plate;

FIG. 39 is a side view taken along line 39—39 of FIG. 36 of the plate of FIG. 36 with an occipital plate stud assembled into the lower occipital plate;

FIG. 40 is a plan view of the under side of an upper occipital plate;

FIG. 41 is a side view of an upper and lower occipital plate assembled together, taken along a line similar to that of 39—39 in FIG. 36;

FIG. 42 is a plan view of an occipital plate stud; and

FIG. 43 is a side view taken along line 43—43 of FIG. 42 of the stud of FIG. 42.

DETAILED DESCRIPTION

The system of the present invention relates to a fixation system which comprises bone screws, saddles, rods, clamps and nuts, all uniquely structured for use in the cervical spine region. Fracture dislocations and dislocations of the cervical spine are indications in which the system of the present invention are likely to be of most benefit. The screw and rod system of the present invention would prevent virtually all motion in the spinal segments instrumented. Two or more segments may be instrumented and stabilized, if desired. If a patient has a severe fracture of the lateral mass of a cervical vertebra, a broken segment may be skipped, and three segments fused together. Cross-linking may be used over the skipped segment to prevent rotation in cases of excessive instability. If there are multiple laminar fractures, the system of the present invention may be used since there is no limit to the number of levels which can be stabilized. Attachment to the occipital bone at the skull may also be done safely and efficiently.

If anterior decompression is necessary, due to retropulsed disc material or bone, the system of the present invention may be assembled posteriorly first, thus providing immediate fixation. The surgeon may then proceed anteriorly, removing disc material and grafting bone as necessary. In degenerative cervical disease, often dramatic posterior decompression is necessary in order to decompress the nerves adequately. The system of the present invention may be used to stabilize the spine after these procedures. In laminoplasty much of the external fixation with casts or braces can be eliminated by use of the fixation system of the present invention. Usually a light neck brace or soft collar is sufficient.

In addition to the foregoing, the system of the present invention may be used in the repair of a swan neck deformity. This deformity results from extensive posterior decompression.

The system of the present invention, although intended for use primarily in the cervical spine, may be extended into the upper thoracic spine. For example, with pathology at C7 or T1, the screws may be placed in the uppermost vertebrae of the thoracic spine and also in the cervical spine, even though there is a rather marked curvature in this area. The rods can be contoured to fit the locations of the screws and saddles in any position or location. The applications and principles of the present invention are described in detail below.

Figure 1:
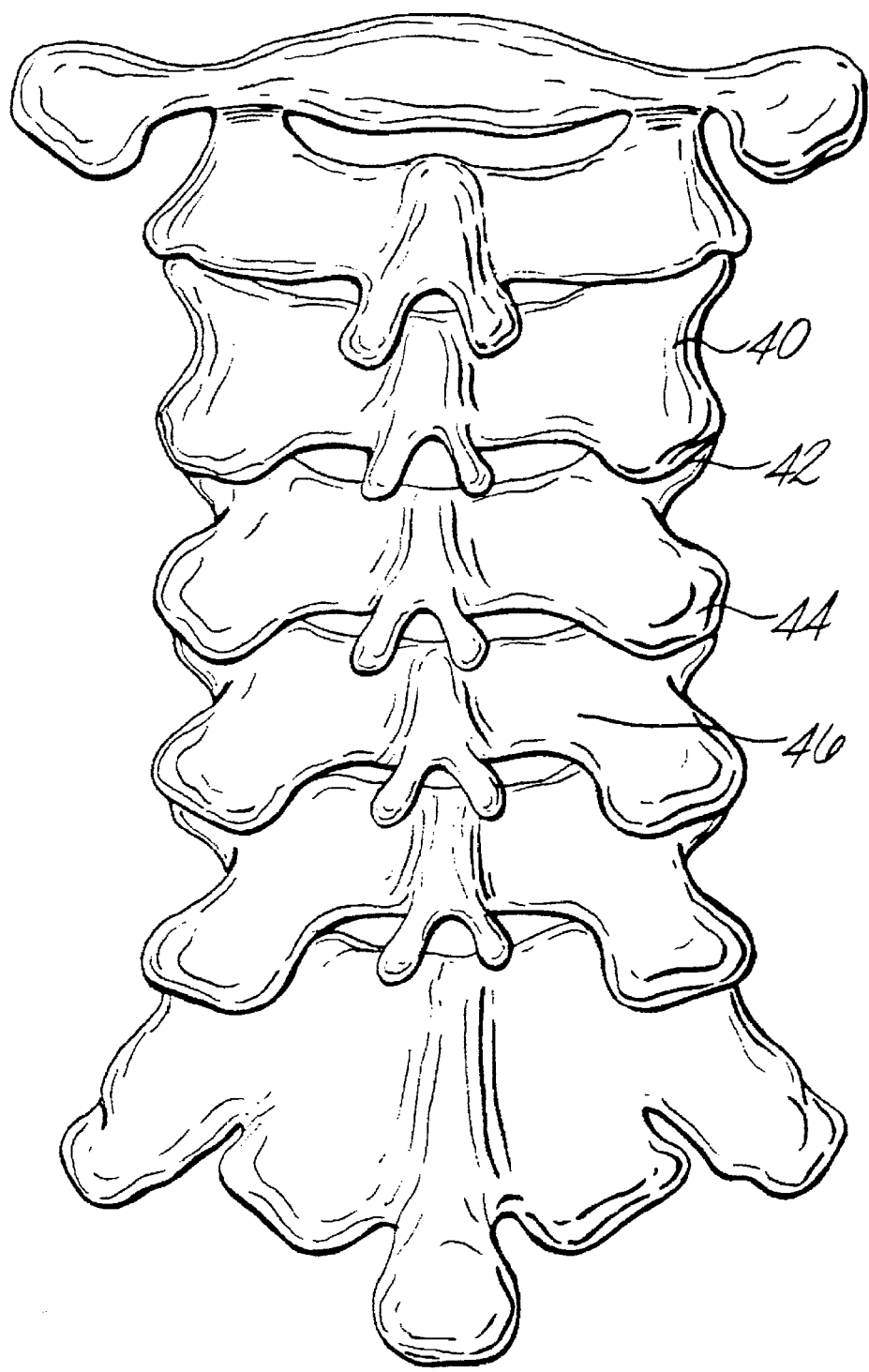
FIG. 1 is a diagrammatic posterior view of the cervical spine.
Figure 2:
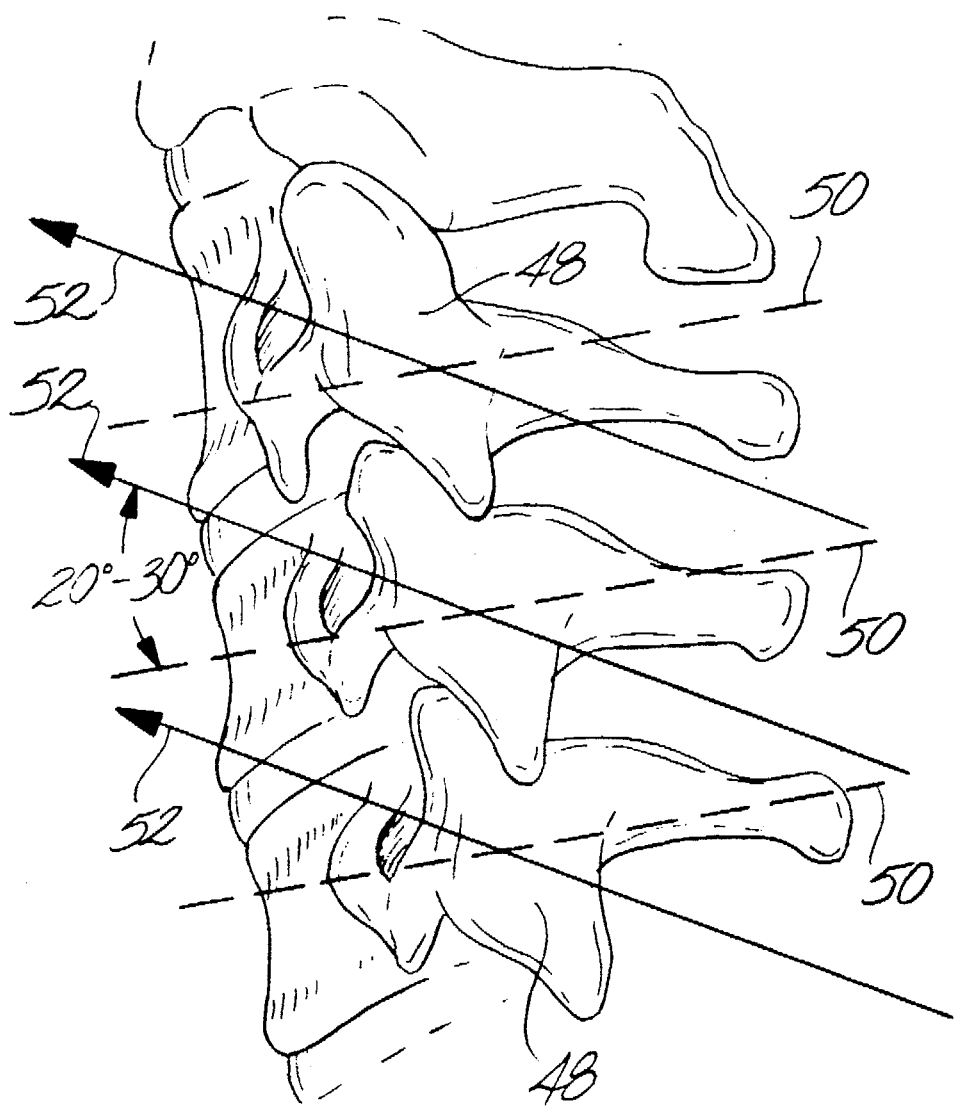
FIG. 2 is a diagrammatic side view of the cervical spine illustrating the cranial-ward orientation of the desired bone screw locations.
Figure 3:
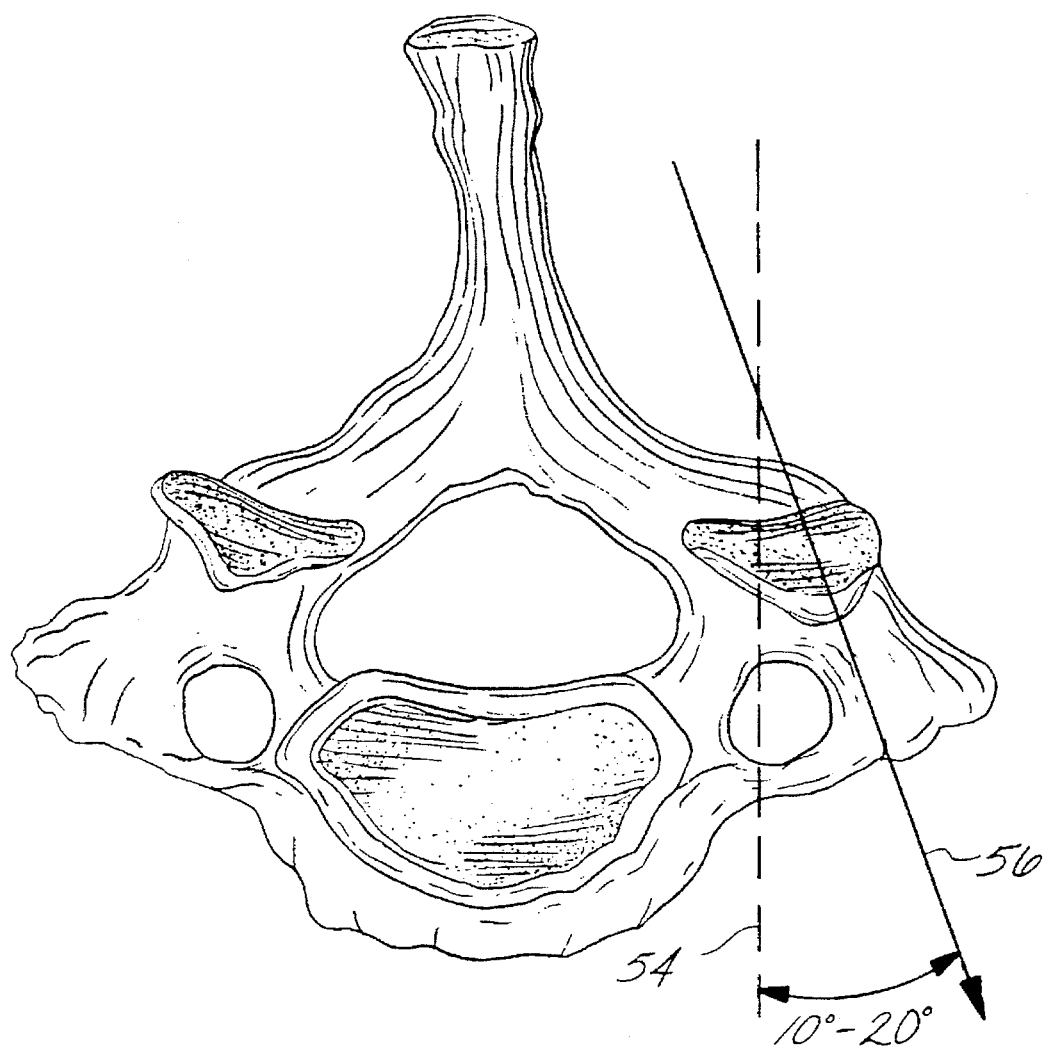
FIG. 3 is a superior sectional diagrammatic view illustrating the lateral orientation of the bone screw locations.

FIG. 1 illustrates the cervical spine from C1 to C7. Labelled in the drawing are the lateral mass 40, the superior facet 42, the inferior facet 44 and the lamina 46. FIG. 2 illustrates the angle between the outer surface 48 of the lateral mass and the transverse left to right axis of the cervical spine, as indicated by the dotted line 50. It is apparent that there is greater bone mass at a cranial-ward angle than along the transverse axis 50. Thus, in accordance with the present invention, the bone screws, described in detail below, are installed in the lateral mass at a cranial-ward angle of between 20° and 30°, the angle between the transverse axis 50 and line 52. In addition, in accordance with the present invention the bone screws are also angled lateral-ward between 10° and 20° as indicated in FIG. 3, the angle between dotted line 54 (representing the transverse axis front to back) and solid line 56.

Figure 4:
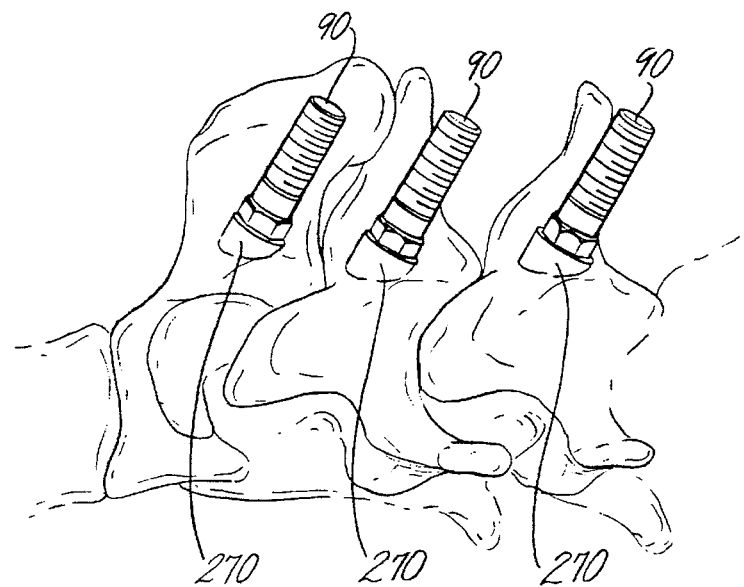
FIG. 4 is a perspective view illustrating the location of the bone screws in accordance with this invention.
Figure 5:
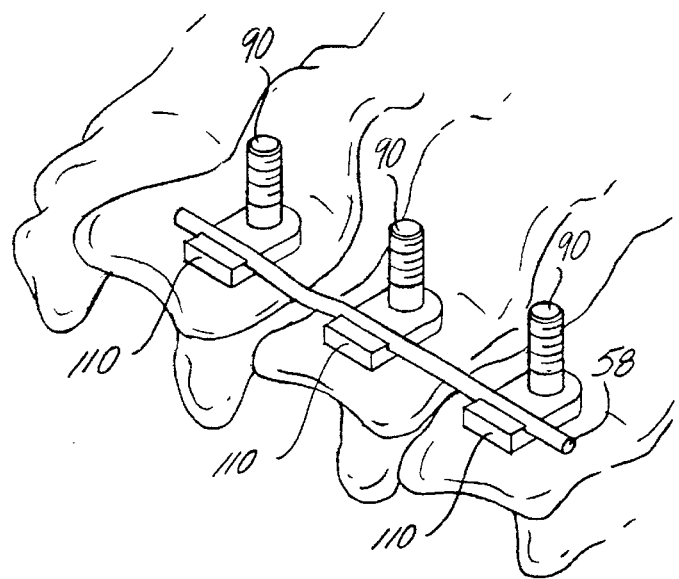
FIG. 5 is a perspective view illustrating the assembly of a rod on a lower saddle in accordance with the present invention.
Figure 14:
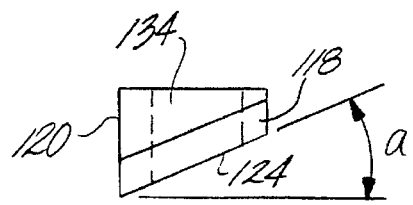
FIG. 14 is an end view taken along the line 14—14 of FIG. 11.
Figure 15:
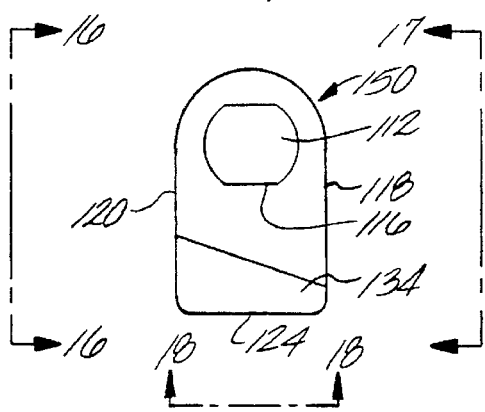
FIGS. 15, 16, 17, and 18 are views similar to FIGS. 11, 12, 13 and 14 but illustrating a lower right hand saddle.
Figure 16:
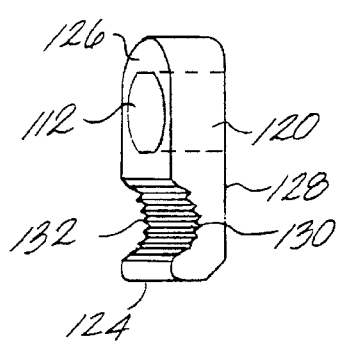
Figure 17:
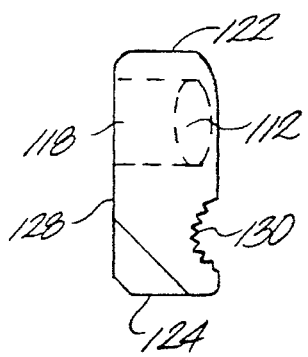

FIGS. 4, 5, 6, 7 & 8 illustrate the orientation and general sequence of installing the fixation system of the present invention. As illustrated in FIG. 4, bone screws 90, described in detail below, are placed in the lateral mass, angled as described above. A spacer 270, described in detail below, has also been installed to raise the bone screws to a desired elevation above the plane of the bone. Bone screws are inserted on each side of the cervical spine. Following insertion of the bone screws, a lower saddle 110 (a lower left hand saddle) or 150 (a lower right hand saddle), which is described in detail below, is assembled over the bone screw, as shown in FIG. 5, and a rod 58 is placed in the lower saddle. If desired a mastering procedure described in U.S. Pat. No. 4,653,481 may be used to configure the rod curvature.

The next step involves assembling an upper saddle 190 (an upper left hand saddle) or 230 (an upper right hand saddle) over the bone screw and rod, as shown in FIGS. 6, 7 & 8. The entire assembly is held together by a locking assembly 60 which operates to bolt the upper and lower saddles onto the rod and to secure the saddles to the bone screw. Each of the components of the fixation device are described in detail below.

Referring to FIGS. 9 and 10, the details of the bone screw 90 are illustrated. The bone screw and other components of the present invention are preferably made of 316 LVM steel, although any other appropriate material for surgical implantation, of equivalent strength, may be used. In a preferred embodiment, the bone screw includes a longitudinal axis and a first threaded end 92 for screwing into the cervical vertebra. Adjacent to the first threaded end is a flange section 94 and a clamp receiving section 96 is adjacent to the flange. Located on an end remote from the threaded end 90 is a second threaded end 98. The portion of the bone screw from the flange 94 to the end of the threaded end 98 is generally of a fixed dimension to accommodate the half-saddles and locking mechanism. Typically this dimension is approximately 10 mm in length, with a diameter of about 3.5 mm. The length of the bone screw from the flange to the free end of the first threaded section 90 may vary from about 10 to 19 mm with a major thread diameter of about 3.5 mm and a minor thread diameter of about 2.5 mm.

The flange diameter is about 5.3 mm and thus extends radially beyond the outer diameter of the threaded end 92. A portion 100 of the flange facing the first threaded section 90 is tapered, as shown. The flange is oriented in a plane which is perpendicular to the long axis of the bone screw. Located between the flange and the threaded end 98 is a non-threaded cylindrical section 102 which has a diameter greater than the diameter of the threaded section 98 but smaller than the diameter of the flange. The cylindrical section acts as a clamp receiving section for the upper and lower half saddles. The clamp receiving section includes spaced exterior flat sections 104 and 106 which mate with internal flat sections on the lower saddle. These flat sections also permit the use of an appropriate tool to thread the bone screw into the lateral mass of the vertebrae.

FIGS. 11, 12, 13, and 14 illustrate a lower left hand saddle 110 which includes an unthreaded aperture 112. The aperture has internal flat sections 114 and 116 which mate with the flat sections 104 and 106 on the bone screw preventing rotation of the lower saddle relative to the bone screw when the fixation system is assembled. The lower saddle includes side faces 118 and 120, which are generally flat, a curved rear face 122, a front face 124 and top and bottom faces 126 and 128, respectively.

Located in the top face 126 and between the aperture 112 and the front face 124 is a groove, or rod receiving half aperture, 130 on which a rod is received. The groove is preferably serrated, as indicated at 132, the serrations extending axially from one side face to the other to mate with serrations on the rod, which is described in detail below.

The bottom face 128 of the lower saddle is generally flat and abuts the flange 94 of the bone screw when assembled on the bone screw, i.e., this face is oriented in a plane which is perpendicular to the long axis of the bone screw. The top face 126 of the lower left saddle is oriented in a plane which is at an angle to the bottom face 128. Thus, the axial dimension of side face 118, of about 2.1 mm, is less than the axial dimension of side face 120, of about 4.8 mm, as measured along the long axis of the bone screw, the rear face forming a gradual transition section whose axial dimension progresses from that of side face 118 to that of side face 120. Accordingly, the axial dimension from the bottom of the groove 130 to the bottom face along side face 118 is less than the axial dimension from the bottom of the groove 130 to the bottom face along side face 120.

This geometry places the groove at an inclined orientation which is essentially parallel to the angular orientation of the top face of the lower saddle, i.e., the plane of the groove is angularly oriented with respect to the long axis of the bone screw. In order to avoid sharp and bulky sections which may contact and damage the bone of the vertebrae, a portion 134 of the bottom face 128 includes a taper which is narrow at the end adjacent to side face 118 and broader adjacent to side face 120 and forms a transition section from the top face to the front face 124. As a result the front face 124 is a relatively narrow section, see FIG. 14, which is angularly oriented, represented by angle "a," in the same plane as the top face. The angle "a" is between about 10° to 25°, with 12° or 22° being preferred.

Figure 18:
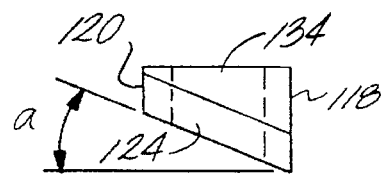
Figure 19:
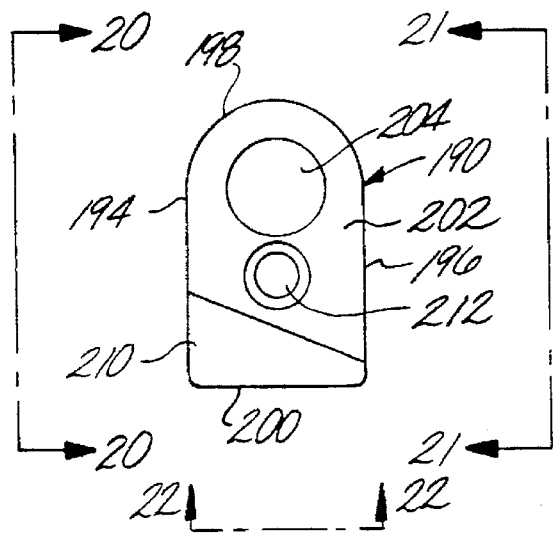
FIG. 19 is a plan view of the top surface of an upper left hand saddle.
Figure 20:
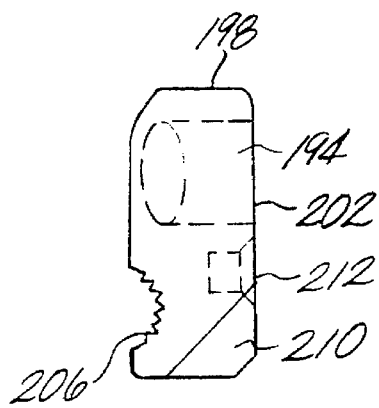
FIG. 20 is a side view taken along line 20—20 of FIG. 19.
Figure 21:
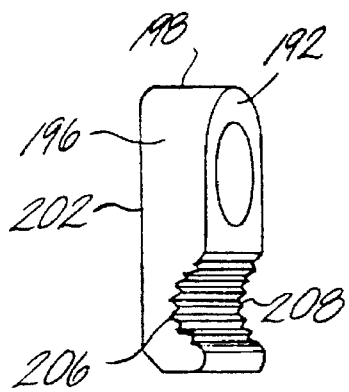
FIG. 21 is a side view taken along line 21—21 of FIG. 19.
Figure 22:
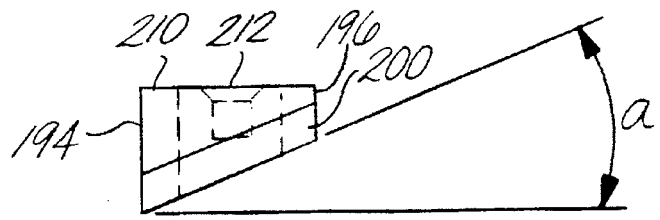
FIG. 22 is a side view taken along line 22—22 of FIG. 19, showing the front face.
Figure 29:
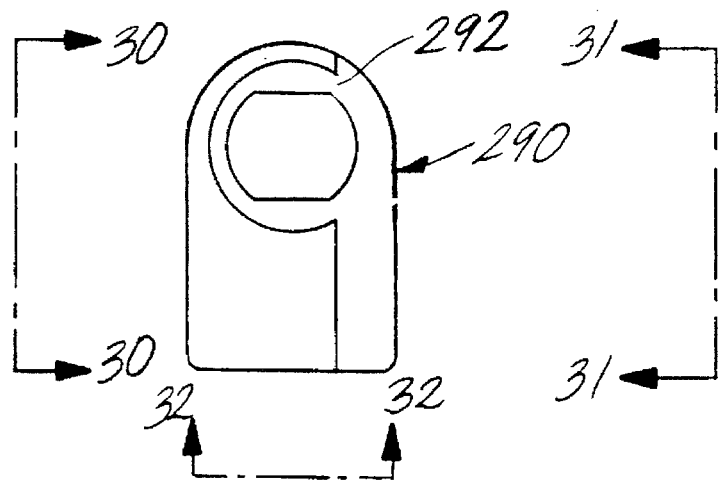
FIGS. 29, 30, 31, and 32 are views similar to FIGS. 11, 12, 13, and 14 but illustrating a lower left hand saddle with an integral spacer in accordance with the present invention.
Figure 30:
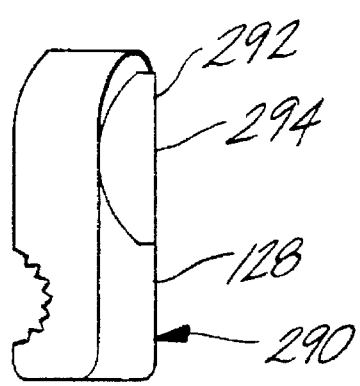
Figure 31:
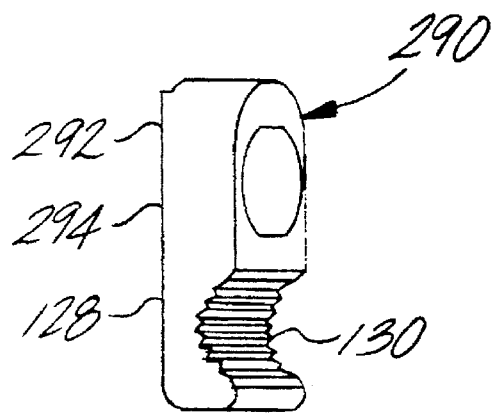
Figure 32:
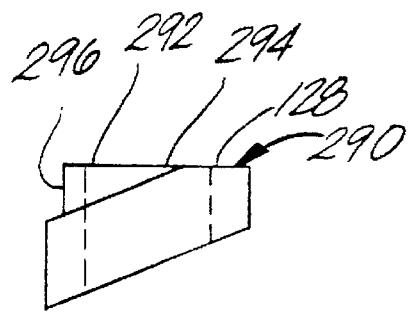

In FIGS. 15, 16, 17 and 18, a lower right hand saddle 150 is illustrated. The lower right hand saddle is basically the same as the lower left hand saddle already described, except that the angular orientation is reversed. In these figures, the same numbers are used to describe similar parts as described in FIGS. 11, 12, 13 and 14. In this form face 118 has a greater axial length than face 120, while the top face 126, as illustrated in FIG. 18, is oriented in an opposite angular orientation as compared to face 126 of FIG. 14. Therefore, left hand half-saddles are used for installation on the left hand side of the vertebrae and right hand half-saddles are installed on the right hand side of the vertebrae, thus allowing a common angular displacement, cranial-ward, of the fixation device.

A upper left hand saddle 190, of one embodiment of the present invention, is illustrated in FIGS. 19, 20, 21 and 22. The upper saddle includes a bottom face 192 adapted to be positioned in facing relation with the top face 126 of the lower saddle, side faces 194 and 196, a curved rear face 198 and a front face 200 and a top face 202. The upper saddle includes an unthreaded generally circular aperture 204 which aligns with the aperture of the lower saddle and when the assembly is place over the end 98 of the bone screw. There are no interior flats in aperture 204.

Located in the bottom face 192 and between the aperture 204 and the front face 200 is a groove, or rod receiving half aperture, 206 on which a rod is received for clamping. The groove 206 is preferably serrated, as indicated at 208, the serrations extending axially from one side face to the other to mate with serrations on the rods when the fixation device is assembled together.

The top face 202 of the upper saddle is generally flat and is oriented in a plane which is perpendicular to the long axis of the bone screw and generally parallel to the lower or bottom face 128 of the lower saddle. The bottom face 192 of the upper left saddle is oriented in a plane angularly disposed with respect to the top face 202, but in an angular orientation for a mating fit with the face 126 of the lower saddle. Thus, the axial dimension of side face 196, of about 2.1 mm, is less than the axial dimension of side face 194, of about 4.8 mm, as measured along the long axis of the bone screw, the rear face 198 again forming a gradual transition section whose axial dimension progresses from that of side face 196 to that of side face 194. Accordingly, the axial dimension from the bottom of the groove 206 to the top face along side face 196 is less than the axial dimension from the bottom of the groove 206 to the top face along side face 194.

This geometry, in effect, places the groove 206 in an inclined orientation which is essentially parallel to the angular orientation of the top face 126 of the upper saddle, i.e., the plane of the groove is angularly oriented with respect to the long axis of the bone screw. In order to avoid sharp and bulky sections which may irritate the neck muscles of a patient when the fixation device is installed, a portion 210 of the top face 202 includes a taper which is narrow at the end adjacent side face 196 and broader adjacent side face 194 and forms a transition section from the bottom face 192 to the front face 200. In effect, the front face 200 is a relatively narrow section, see FIG. 22, which is angularly oriented in the same plane as the top face at an angle "a". Angle "a" is between about 10° to 25°, with 12° or 22° being preferred.

The angular orientation of the rod receiving grooves with respect to the long axis of the bone screws also results in a comparable angular orientation of the rod with respect to the long axis of the bone screws. Typically, the rods, made of the material already described, are about 3.1 mm in diameter and may vary in length from about 25 mm to at least about 100 mm as required for the fixation procedure being performed. The outer surface of the rod is serrated along its length, having for example 28 teeth and the serrations match those on the grooves of the saddles.

Unlike the lower saddle, the upper saddle 190 in this embodiment of the invention has provided in the top face 202 a blind aperture 212, the latter located between aperture 204 and the inclined portion 210 of the top face. In one embodiment of the present invention, described in detail below, a locking assembly 60 comprises a locking washer wherein a locking tang 220 of a lock washer is received in this aperture 212. As illustrated on an upper right hand saddle, in FIGS. 23, 24, and 25, the lock washer 214 is a separate item assembled between the upper saddle 230 and a nut 260, see FIG. 7. The upper right hand saddle is basically the same as the upper left hand saddle already described, except that the angular orientation is reversed. In these figures, the same numbers are used to describe similar parts as described in FIGS. 19, 20, 21 and 22.

In the assembly procedure one tang 220 of the washer is deformed into the blind aperture, a nut 260 is threaded over the distal end of the bone screw and tightened and the remaining tangs are deformed to grip the sides of the nut, see FIG. 26. The lock washer 214 includes three tangs, 216 and 218 which are deformed upwardly, and 220 which is deformed downwardly and received in the blind aperture 212. Tang 220 effectively attaches the lock washer 214 to the upper saddle. When tangs 216 and 218 are deformed upwardly they lock the nut in place and prevent it from loosening after installation.

In one embodiment of the present invention as seen in FIG. 26, once the mating saddles, here the left hand saddles 150 and 190, are mounted on the bone screw 90 and bolted together by the nut 260 and lock washer 214 which, as mentioned, may be fixed to the upper saddle, as shown in FIGS. 23, 24 and 25, the assembly is essentially completed. In the assembled form the tangs 216 and 218 are deformed around a nut 260 threaded on the end 98 of the bone screw. Since the lower saddle includes interior flats 116 and 114 which mate with flats 106 and 104 on the bone screw, the lower saddle is prevented from rotating relative to the bone screw. The upper saddle is prevented from rotating relative to the lower saddle due to the inclined mating faces 126 and 192. Moreover, since the saddles, which form a rod clamp are bolted against the shoulder 94 of the bone screw, as contrasted to being bolted against the bone of the cervical spine, there is substantial strength in the completed assembly. Further, the rod(s) are firmly secured in the clamp formed by the mating saddle assemblies which form a rod receiving aperture since the grooves, or rod receiving half apertures, and the rod are dimensioned for good purchase and serrated to prevent rod rotation relative to the clamp. The above is true of both the right and left hand configurations.

The lock nut illustrated FIG. 7 is a hexagonal nut, but other nuts may be used. In a another embodiment of the present invention, illustrated in FIG. 6, the locking nut is an acorn nut with a smooth, curved top surface to reduce possible irritation to the muscles which cover the fixation device when it is installed in a patient.

Occasionally, it may be necessary to raise the saddle clamp assembly above the level of the cervical bones to allow clearance of the bone structure surrounding the saddle clamp assembly and to reduce the amount of bending of the rod which connects to the saddle clamps. One way of achieving this is by the use of a cervical spacer 270 illustrated in FIGS. 27 and 28. The assembled location of the spacer is shown in FIG. 4, between the tapered under surface of the screw flange 94 and the cervical bone structure. This spacer, made of material already described, is generally cylindrical in shape and includes an aperture 272 through which the bone screw passes. A counterbored section 274 mates with the curved under surface 100 of the bone screw flange. Angularly oriented face 276 normally rests against the bone, the angle "b" being between 15° and 35°. The spacer provides support for the portion of the bone screw which extends above the bone and provides clearance, where desired.

A preferred embodiment of clamp assembly for providing a clearance is illustrated in FIGS. 29, 30, 31 and 32 which illustrate a lower left hand saddle assembly 290, which in all essential respects is the same as the lower left hand saddle of FIGS. 11, 12, 13 and 14, save for the presence of an integral spacer extension 292. As shown, the spacer 292 is located on the bottom face 128 and includes a top surface 294 which is essentially flat and planar and oriented in a plane which is perpendicular to the long axis of the bone screw. In installation, the top surface bears against the flange 94 of the bone screw, thus raising the groove 130 a distance corresponding to the vertical height 296 of the extension. The vertical height 296 may be varied as needed. It is understood that a lower right hand saddle having an integral spacer (not shown) could also be used.

In a preferred form, all parts thus far described are processed to break all sharp edges and are electropolished and passivated. The parts described may be sterilized prior to use by any of the known sterilization procedures.

In use, the screws are located in the proper position, as determined by the surgeon. The spacer may be placed on the bone with the bone screw passing through the spacer. The lower saddle is assembled over the bone screw. Several screws and saddle assemblies may be installed. If the rod is to be configured, the mastering technique referred to above may be used. The properly configured final rod is then placed in the groove(s) and the upper saddle assembly is placed over the lower saddle and secured in place by any of the several devices already described.

In another embodiment of the present invention, illustrated in FIG. 8 the cervical fixation device is designed to minimize or reduce irritation to the neck muscles which overlay the system once it has been installed. In the system described above, the locking nut extends beyond the clamping assembly. In some instances, the length of the screw-clamp assembly tends to cause muscle irritation after implantation. In this embodiment of the invention, a sleeve nut fits into a recess on the upper surface of an upper half-clamp. The novel sleeve nut in this embodiment of the present invention greatly reduces the overall axial length of the screw-clamp assembly, resulting in a low profile and smooth upper surface of the fixation system which reduces the likelihood for the system's causing the formation of a painful bursa. The upper and lower saddle and bone screw are similar to those described above and will only be described briefly here to point out the differences. The same numbers are used for parts that are unchanged from the parts described previously.

The lower saddles are essentially the same as described above and illustrated in FIGS. 11–18.

Figure 33:
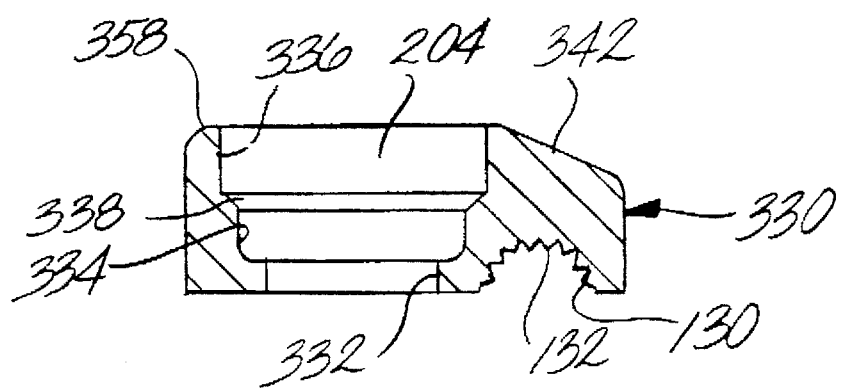
FIG. 33 is a side view of another embodiment of an upper saddle for use in the present invention.

An upper saddle 330 illustrated in FIG. 33, is provided with an aperture 204 for receipt on the upper threaded end 98 of the bone screw 90. The axial length of the upper-half clamp is greater than that of the upper threaded end 98 of the bone screw so that, when assembled, none of the threaded portion extends beyond the upper saddle 330.

The internal diameter of the upper saddle aperture is stepped. A lower section 332 has a diameter such that, when placed on the bone screw, the upper saddle will fit securely against the cylindrical section 102 of the bone screw. An intermediate section 334, which abuts the lower section, has an intermediate diameter which is greater than the diameter of the lower section. Adjacent the intermediate section is an upper section 336, which has a diameter larger than that of the intermediate section. The intermediate and upper sections are separated by a chamfer line 338. When assembled, the intermediate and upper sections accommodate a sleeve nut 340, illustrated in FIG. 34 which is described in detail below.

Figure 34:
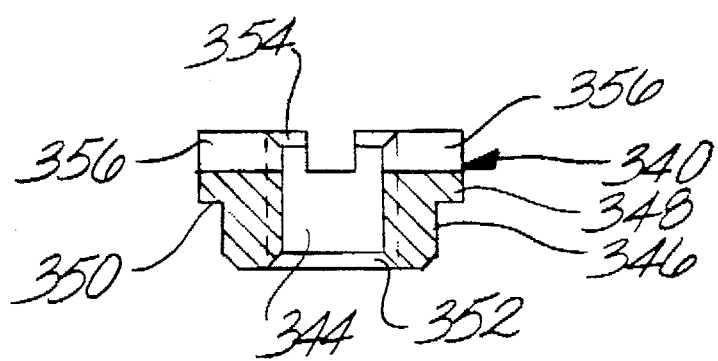
FIG. 34 is a sleeve nut for use in clamping the upper saddle illustrated in FIG. 33 to the bone screw.

The upper saddle also includes an arm 342 in which is a groove 130, laterally of the aperture 204. The groove is serrated along its length, as indicated at 132, for mating and gripping the serrated rod. The geometry of the upper saddle is the same as described for the upper half saddles described above and places the groove at an inclined orientation which is essentially parallel to the angular orientation of the top face of the lower saddle, i.e., the plane of the groove is angularly oriented with respect to the long axis of the bone screw. When assembled, the serrated surfaces of the upper and lower saddles are in facing relation to each other and mate with, and firmly grip, the serrated rod. When assembled, the lower and upper saddles are placed on the bone screw, as described above. A sleeve nut is used to hold the lower and upper saddles in place on the bone screw flange 94 and to ensure a firm grip on the rod. The sleeve nut is illustrated in FIG. 34. The sleeve nut 340 has an aperture 344, which is threaded so that it mates with the threaded portion 98 of the bone screw.

The exterior of the sleeve nut is of different diameters. At the lower end of the sleeve nut, the diameter of the sleeve nut 346 is at its smallest and is sized such that the sleeve nut will fit into the stepped region 334 of the upper saddle. At the upper end of the sleeve nut, and adjacent the small-diameter portion 346, is a large-diameter portion of the sleeve nut 348. A fillet radius 350 is located at the juncture of the small- and large-diameter portion of the sleeve nut. The large-diameter portion is sized so that it will fit into the stepped region 336 of the upper saddle, thus holding the upper saddle and the lower saddle securely in place when the sleeve nut is screwed onto the bone screw. The stepped interior of the upper saddle allows a distribution of the force conferred by the sleeve nut on the upper saddle over a larger area. A chamfer line 352 is locate at the bottom of the sleeve nut.

The top face 354 of the sleeve nut includes four radial notches 356, placed at equal distances from each other. The notches align with prongs of a driver, not shown, so that the surgeon can more easily attach the sleeve nut to the bone screw.

In use, the lower saddle is assembled over an bone screw, and then, after the rod is in position, the upper half-clamp is installed. The sleeve nut is then threaded on the upper threaded-end portion of the bone screw and tightened down, using a driver. The prongs of the driver are mated with the notches of the sleeve nut and the driver is then used to tighten the sleeve nut into the upper saddle. The sleeve nut, when tightened down, is completely contained within the aperture 204, leaving exposed a small portion of the upper edge of the face 358 of the upper saddle.

After the sleeve nut is in place, the exposed portion of the face 358 is crimped at one point along its periphery corresponding to one of the radial notches. The crimp ensures that the sleeve nut is firmly locked in place and that undesired rotation of the sleeve nut is inhibited.

In the event that some adjustment, and hence removal of the sleeve nut is necessary, the crimp is easily overcome by using the driver to remove the sleeve nut, and the sleeve nut is unscrewed to release the upper and lower saddles. After any required adjustment has been made, the screw-and-clamp assembly is secured in place, as described above.

The advantage of the low profile cervical fixation system of the present invention is, that the axial length (height) of the screw-clamp assembly is greatly reduced, when compared to the height of other screw-clamp assemblies, since the axial length of previous screws had to be of a dimension sufficient to accommodate at least one nut and locking washer above the clamp. The height of the screw-clamp assembly as installed increased the probability of muscle irritation by the clamp assembly. Also, the installed fixation system has a top surface which is in a single plane which reduces muscle irritation. In one embodiment of the present invention, the sleeve nut fits into a recess on the upper surface of the upper saddle, greatly reducing the overall axial height of the bone screw above the upper saddle. This low profile of the fixation system reduces the likelihood of the system's causing the formation of a painful bursa.

Figure 35:
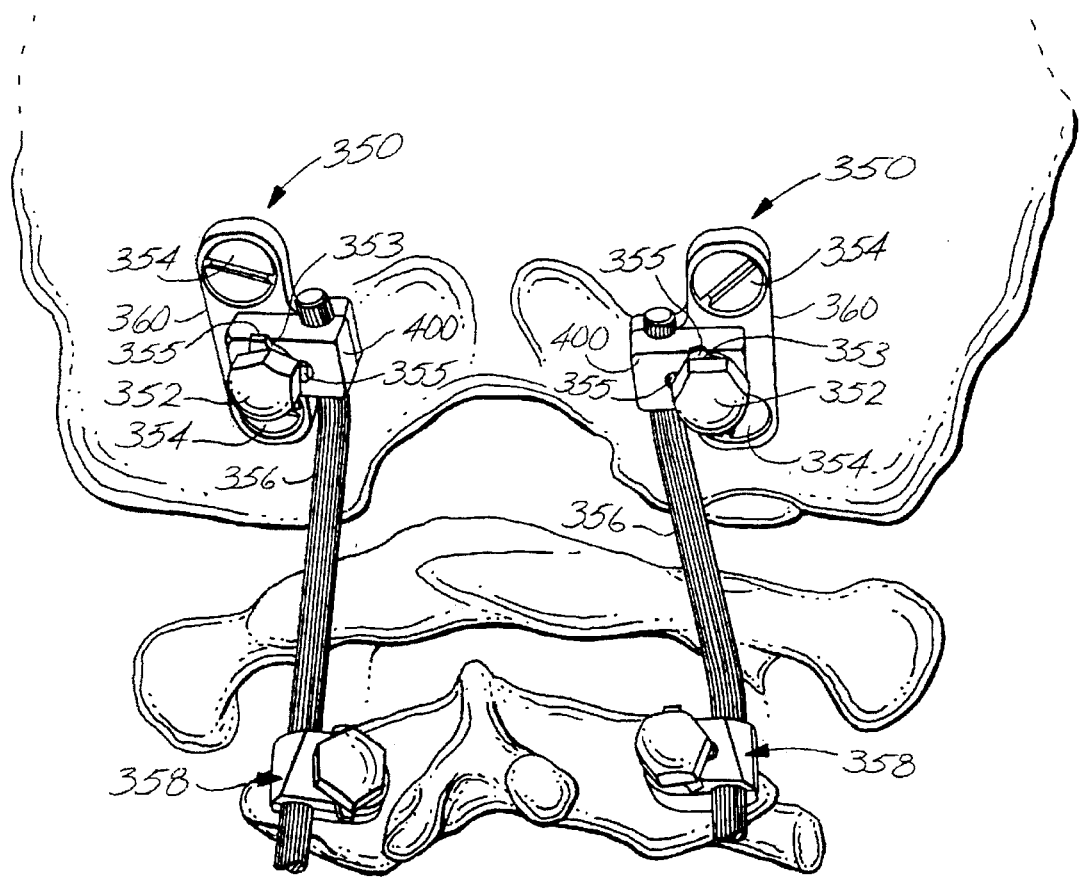
FIG. 35 is a perspective view illustrating an occipital plate assembly attached to the occipital squama, on either side of the external occipital crest.

In another embodiment of the present invention the cervical fixation system is used to treat damage to the spine in the region of the first (atlas) or second (axis) cervical vertebra. In such cases the fixation device is attached at one end to the cervical vertebra, as described above. The other end is attached to the occipital squama, on either side of the external occipital crest, by an occipital plate assembly 350, as shown in FIG. 35. The occipital plate assembly comprises a lower occipital plate 360 (illustrated in FIGS. 36, 37, 38, 39 and 41), an upper occipital plate 400 (illustrated in FIGS. 40 and 41), an occipital plate stud 420 (illustrated in FIGS. 42 and 43), a nut 352, attached to the occipital plate stud, and screws 354 attaching the lower occipital plate to the occipital squama. A serrated rod 356 connects the occipital plate assembly to the cervical assembly 358.

FIGS. 36, 37, 38 and 39 illustrate a lower occipital plate 360. The lower occipital plate is a generally rectangular shaped plate 362 with an outwardly extending arm 364 perpendicular to the rectangular shaped plate, and located at the middle of one of the long sides of the rectangle. The arm includes a groove 366 (see FIG. 39). The groove is serrated along its length, as indicated at 368, for mating and griping the serrated rod 356.

At either end of the rectangular shaped plate are apertures 370 for receiving screws 354 and for attaching the occipital plate to the occipital squama. Each aperture has a greater diameter 371 at an upper side of the plate that the diameter 373 at a lower side of the plate. The different diameters of the aperture allow the "V" shaped head of the screw to seat into the aperture and to hold the lower occipital plate onto the occipital sguama.

Located between the apertures 370, adjacent to the arm, is a generally cylindrical third aperture 372 (see FIG. 37). One sidewall 374 of the aperture 372 is flattened (see FIG. 36). On an under surface of the plate the aperture is counterbored 376. The counterbored aperture 372 acts to seat a threaded occipital plate stud 420. The stud has a flat section 430 on one side for mating with the flattened sidewall of aperture 372. The flat sides act to correctly locate the stud in aperture 372 and to prevent it rotating relative to the lower occipital plate.

Located on the under side of the lower occipital plate are channels 378. The channels allow the lower occipital plate to flex so that it can be molded to the gentle curve of the occipital squama and thus lay flat against and conform to the occipital squama surface.

Stud 420, illustrated in FIGS. 42 and 43, comprises a threaded end 422 which is adjacent to a non-threaded section of similar diameter 424. The non-threaded section abuts a shoulder 426 which separates the non-threaded section 426 from a larger diameter second non-threaded section 428. The diameter of the non-threaded section 428 is dimensioned so that it will fit "snugly" into aperture 370 when the plate stud is assembled into the lower occipital plate. Non-threaded section 428 includes the flat section 430, described above. Adjacent to non-threaded section 428 is a second shoulder 432 which has an increasing tapered diameter greater than that of the non-threaded section 428 as it extends away from that section. Shoulder 432 is of a larger diameter than the diameter of the aperture 372. The counterbored section of the aperture 372 acts to seat the shoulder 432. The larger diameter of shoulder 432 prevents the stud from slipping through the aperture 372 when the stud and lower occipital plate are assembled (see FIG. 38).

The upper occipital plate 400, illustrated in FIGS. 40 and 41, is a rectangular shaped plate with an aperture 402 at one end of the plate. The diameter of aperture 420 is dimensioned so that it will fit "snugly" onto non-threaded section 424 when the upper occipital plate is assembled onto the plate stud. Located at the other end of the upper plate, on an under surface of the upper plate, is a groove 404. When the upper plate is placed on the lower plate the groove 404 aligns with the groove 368 of the lower plate to form a rod receiving aperture for securely gripping the serrated rod 356.

In use, the occipital plate stud is slipped into the aperture 372 in the lower occipital plate so that it extends up away from the occipital squama by aligning flat sections 430 and 374. The lower occipital plate is then attached to the occipital squama using screws 354. Once the lower plate is firmly attached to the occipital squama, the upper plate is placed onto the stud and aligned to bring the groves 368 and 404 in facing relation to form a rod receiving aperture. A rod is placed into the rod receiving aperture and the upper plate is tightened to the lower plate.

In one embodiment of the present invention the upper plate is clamped to the lower plate by screwing an acorn nut 352 onto the threaded end of the stud. The acorn nut is locked into place with a lock washer 353 which includes three deformable tangs 355 (only two of which are shown in FIG. 35). Two of the tangs are deformed upwardly, and one is deformed downwardly and received in the blind aperture 406 (illustrated in FIG. 41). The downwardly deformed tang effectively attaches the lock washer to the upper plate. The upwardly deformed tangs lock the nut in place and prevent it from loosening after installation. Such a nut and lock washer are described above in relation to FIGS. 22, 24, 25, and 26, and are identical to the nut and lock washer for attachment of the upper plate.

In an alternate embodiment, the locking assembly comprises a low profile system which includes a locking nut which fits into a recess on the upper surface of the upper plate. Such a low profile system is described in conjunction with FIGS. 33 and 34, and a similar system can be used for attachment of the upper plate. In the case of a low profile system, the upper plate is modified to include the stepped sections (as illustrated in FIG. 33) into the upper surface of the upper occipital plate, around aperture 402. The upper plate is then attached to the plate stud with a nut similar to that illustrated in FIG. 34.

It is apparent from the foregoing detailed description that the present invention has many advantages over the support systems and methods of the prior art as applied to the cervical spine. It will be apparent that various modifications may be made to the support system and methodology of the present invention by those skilled in the art without departing from the scope of the appended claims.

What is claimed is:

1. A cervical spine fixation system comprising:

a bone screw, having a longitudinal axis, for implanting in cervical vertebrae of the spine and for accommodating a clamping assembly;

a clamping assembly mounted on the bone screw, wherein the clamping assembly comprises;

an upper saddle comprising a rod receiving half-aperture angularly oriented at a predetermined fixed angle with respect to a plane perpendicular to the longitudinal axis of the bone screw to thereby maintain a rod received into the rod receiving aperture in generally parallel alignment with the plane of the spinal column wherein the predetermined fixed angle ranges from about 10° to about 25°;

a lower saddle comprising a rod receiving half-aperture angularly oriented a predetermined amount from a plane perpendicular with respect to the longitudinal axis of the bone screw which mates in parallel relation with the upper saddle to form a rod receiving aperture, the mating saddles further comprising an upper and lower surface on each of the upper and lower saddles, an aperture in the upper surface of the upper saddle, and a lock washer having a plurality of spaced tangs mounted on the upper surface of the upper saddle wherein one of the tangs of the lock washer is received in the aperture to secure the lock washer to the upper saddle; and means for attaching the clamping assembly to the bone screw.

2. A cervical spine fixation system comprising:

a bone screw having a longitudinal axis, a first threaded end for implanting into a cervical spine vertebra, a second threaded end, and a flange oriented in a plane perpendicular to the longitudinal axis of the bone screw and between the first threaded end and the second threaded end of the bone screw;

a clamp assembly, having a generally flat bottom face mounted on the second threaded end of the bone screw and supported by the flange, comprising a rod receiving aperture, the rod receiving aperture being angularly oriented at a predetermined fixed angle with respect to the plane perpendicular to the longitudinal axis of the bone screw such that a rod is located in parallel relation to the rod receiving aperture and wherein the predetermined fixed angle ranges from about 10° to about 25° the clamp assembly further comprising an upper and a lower saddle each of which includes parallel side faces at either end of the rod-receiving half aperture wherein the axial dimension of a side face at one end of the rod-receiving half aperture is of a different axial dimension than the side face at the other end of the rod-receiving half aperture;

the rod, having a longitudinal axis, and received in the rod receiving aperture; and means to secure the clamp assembly to the bone screw whereby the rod is securely fixed in the rod receiving aperture.

3. A cervical spine fixation system comprising:

a bone screw comprising:
 a longitudinal axis;
 a first threaded end for implantation into a cervical spine vertebra;
 a clamp receiving section including a rotation preventing means;
 a second threaded end spaced from the first threaded end; and
 a flange between the threaded ends;

a clamp assembly, for mounting on the bone screw, comprising:
 a lower saddle comprising:
  an aperture for mounting the lower saddle on the second threaded end of the bone screw to abut the flange of the bone screw wherein the aperture has a longitudinal axis which is collinear with the longitudinal axis of the bone screw when mounted on the bone screw;
  a clamp rotation prevention means in the aperture for cooperating with the rotation preventing means of the bone screw whereby the lower saddle is fixed against rotation with respect to the bone screw; and
  a rod receiving half-aperture spaced laterally from the aperture and angularly oriented at a predetermined angle with respect to a plane perpendicular to the longitudinal axis of the aperture and wherein the predetermined angle ranges from about 10° to about 25°;
 an upper saddle comprising:
  an aperture, with a longitudinal axis for mounting the upper saddle on the second threaded end of the bone screw wherein the aperture in the upper saddle is alignable with the aperture of the lower saddle; and
  a rod receiving half-aperture spaced laterally from the aperture and angularly oriented at a predetermined angle with respect to a plane perpendicular to the longitudinal axis of the aperture such that the rod receiving half-aperture of the upper saddle is in parallel relation with the rod receiving half-aperture of the lower saddle when mounted on the bone screw; and
 a rod receiving aperture, formed by the mating of the lower and upper saddles, wherein a rod received in the rod receiving aperture is in parallel relation to the rod receiving aperture and angularly oriented at the predetermined angle with respect to a plane perpendicular to the longitudinal axis of the bone screw; and
 means to secure the mating saddles together and against the flange on the bone screw whereby the rod is securely fixed in the rod receiving aperture.

4. A cervical spine fixation system as recited in claim 3 wherein the system comprises a plurality of bone screws forming pairs adapted to be located on each side of the cervical spine.

5. A cervical spine fixation system as recited in claim 3 wherein the mating saddles further comprise a lock washer having a plurality of spaced tangs mounted on the upper surface of the upper saddle wherein one of the tangs of the lock washer is received in the aperture to secure the lock washer to the upper saddle.

6. A cervical spine fixation system as recited in claim 3 wherein the means to secure the mating saddles together and against the flange on the bone screw comprises a sleeve nut, wherein the sleeve nut is substantially recessed into the clamping assembly when the bone screw and clamps are assembled.

7. A cervical spine fixation system as recited in claim 3 wherein the system further comprises a spacer located over the first threaded end of the bone screw.

8. A cervical spine fixation system comprising:

a bone screw having a longitudinal axis, a first threaded end for implanting into a cervical spine vertebra, a second threaded end, and a flange oriented in a plane perpendicular to the longitudinal axis of the bone screw and between the first threaded end and the second threaded end of the bone screw;

a clamp assembly, having a generally flat bottom face mounted on the second threaded end of the bone screw and supported by the flange, comprising a rod receiving aperture, the rod receiving aperture being angularly oriented at a predetermined fixed angle with respect to the plane perpendicular to the longitudinal axis of the bone screw such that a rod is located in parallel relation to the rod receiving aperture and wherein the predetermined fixed angle ranges from about 10° to about 25° the clamp assembly further comprising an upper and lower saddle each of which includes an upper and lower surface, an aperture in the upper surface of the upper saddle, and a lock washer having a plurality of spaced tangs mounted on the upper surface of the upper saddle wherein one of the tangs of the lock washer is received on the aperture to secure the lock washer to the upper saddle;

the rod, having a longitudinal axis, and received in the rod receiving aperture; and means to secure the clamp assembly to the bone screw whereby the rod is securely fixed in the rod receiving aperture.

* * * * *